United States Patent [19]

Lescrenier

[11] 4,242,587
[45] Dec. 30, 1980

[54] PATIENT POSITIONING DEVICE COMPRISING LIGHT PLANES CORRESPONDING TO FIRST, SECOND AND THIRD INTERSECTING REFERENCE PLANES

[76] Inventor: Charles Lescrenier, 660 Crescent Ct., Wauwatosa, Wis. 53213

[21] Appl. No.: 46,436

[22] Filed: Jun. 7, 1979

[51] Int. Cl.² .................. G01N 21/00; H05G 1/62
[52] U.S. Cl. .................................. 250/491; 250/445 T
[58] Field of Search .................... 250/252, 491, 445 T

[56] References Cited

U.S. PATENT DOCUMENTS

| | | | |
|---|---|---|---|
| 4,117,337 | 9/1978 | Staats | 259/491 |
| 4,132,900 | 1/1979 | Smith et al. | 250/491 |
| 4,139,775 | 2/1979 | Williams et al. | 250/491 |

Primary Examiner—Alfred E. Smith
Assistant Examiner—T. N. Grigsby
Attorney, Agent, or Firm—Andrus, Sceales, Starke & Sawall

[57] ABSTRACT

A patient orienting device accurately positions a patient with reference to a source of diagnostic or therapeutic radiation. The planes of light are appliable to the body of the patient and correspond to the sagittal, frontal, and transverse planes of the body. The device includes a first light source establishing a first light plane lying in the sagittal plane. The first light source is typically located at the foot of the patient. A second light souce establishes second and third mutually perpendicular planes of light. The second light source is typically located at the head of the patient. The light source is positioned so that one of the light planes is co-planar with the first light plane and so that the other light plane lies in the frontal plane. A third light source establishes fourth and fifth mutually perpendicular planes of light. The third source lies on one side of the sagittal plane so that the fourth and fifth light planes intersect the first light plane normal to the latter. A fourth light source establishes sixth and seventh mutually perpendicular light planes. The fourth light source lies on the other side of the first light plane so that the sixth and seventh light planes perpendicularly intersect the first light plane. The fourth and sixth light planes lie in the frontal reference plane, along with the second light plane. The fifth and seventh light planes lie in the transverse reference plane.

12 Claims, 9 Drawing Figures

PATIENT POSITIONING DEVICE COMPRISING LIGHT PLANES CORRESPONDING TO FIRST, SECOND AND THIRD INTERSECTING REFERENCE PLANES

BACKGROUND OF THE INVENTION—FIELD OF THE INVENTION

The present invention relates to orienting apparatus utilizing a plurality of light planes for positioning purposes.

BACKGROUND OF THE INVENTION—DESCRIPTION OF THE PRIOR ART

A patient must be accurately positioned with respect to a radiation beam used for diagnosis or therapy in order to achieve a desired degree of effectiveness while minimizing undesirable side effects. Since the radiation beam is not visible to the eye, various targeting devices have been utilized to insure that the beam will impinge the correct portion of the patient. Typically, a reference light pattern is applied to the patient and the patient or radiation source moved until proper positioning is obtained for exposure.

However, such a technique is often less than completely satisfactory. If the patient moves, for example, rolls about an axis normal to the radiation beam, diseased or injured tissue within the body may move substantially out of the radiation beam but little misalignment can be noted. Under these circumstances, the effect of the radiation treatment may be substantially reduced.

If efforts are made to retain the light pattern during exposure to verify positioning, the radiation beam source may block the light, preventing accurate detection of misalignment.

In tomographic imaging, the radiological image is obtained parallel to the beam, rather than normal to it. Many types of targeting devices are incapable of insuring proper positioning of the patient to obtain such images.

Further, it is often desirable to obtain tomographic images parallel to planes not directly identifiable by exterior anatomical landmarks. For example, in neurological tomography, images in planes parallel to the base of the brain are often required. However, the brain base plane is not directly identifiable from the exterior of the skull.

To obtain such images, the orientation of some identifiable anatomic plane such as the orbital meatal plane, which extends along each side of the skull from the canal of the ear to the outer corner of the eye socket, is determined. A correction is then made for the relationship of the orbital meatal plane to the brain base plane, and the tomographic scanner positioned in accordance with the foregoing calculation. However, this tends to be time consuming and subject to inaccuracies.

SUMMARY OF THE PRESENT INVENTION

The present invention relates to a means for rapidly and accurately orienting a patient or radiation beam source so that he/she may be positioned with respect to the radiation beam both before and during exposure. A particular embodiment of the present invention may be used for orientation to obtain images parallel to the plane of the base of the brain.

The device of the present invention orients the patient along first, second, and third mutually perpendicular reference planes of light bearing an established relationship to the source of radiation and corresponding to the sagittal, frontal, and transverse plane of the human body. The device includes first light source means for establishing a first plane of light lying in a first reference plane corresponding to the sagittal plane. The first light source is located at one end of the sagittal plane, typically the foot end. A second light source located at the other end of the sagittal plane establishes second and third planes of light. One of these light planes lies in the sagittal plane, the other light plane lies in a second reference plane corresponding to the frontal plane of the body. With patient lying on a radiological bed, the second and third planes are applied to the top of the skull. The first and second light source means are so positioned with respect to the radiation source so that the planes of light may be applied to the patient during exposure of the patient to the radiation of the source. A third light source means establishes fourth and fifth mutually perpendicular planes which perpendicularly intersect the sagittal reference plane from one side of the latter. The fourth light plane lies in the frontal reference plane. The fifth light plane lies in a third reference plane corresponding to the transverse reference plane of the body. A fourth light source establishes sixth and seventh mutually perpendicular light planes which perpendicularly intersect the sagittal reference plane from the other side. The sixth and seventh light planes also lie in the frontal and transverse reference planes, respectively.

In use, the patient is moved into the intersectioning planes of light. The patient will typically be lying on a radiological table. The planes of light form luminous lines where they intersect the body. The line of the sagittal plane will be formed of the first and second light planes. The line of the frontal plane will be formed from the third, fourth and sixth light planes and the line of the transverse plane will be formed from the fifth and seventh light planes. The individual light planes are joined so as to present a substantially continuous line on the portions of the body to which they are applied. The patient or table is then moved until he/she is properly positioned as indicated by the pattern of lines on the body. With the patient properly oriented, the source of radiation is brought into position and the patient exposed. The first and second light source means are so located that the sagittal frontal line remain rapplied to the patient when the radiation source is positioned for exposure.

In a modification of the patient orienting device, one of the third or fourth light source means is so constructed that one of the light planes serves as a reference plane and the other light plane is arcuately movable with respect to the one plane so as to lie along an anatomic landmark plane of the patient such as the orbital meatal plane. Means are provided for ascertaining the amount of the arcuate movement and thus the position of the orbital meatal plane. From this, the plane of the base of the brain may be located for use in positioning a tomographic imaging apparatus.

DETAILED DESCRIPTION OF THE PREFERRED EMBODIMENT

Figure 1A:
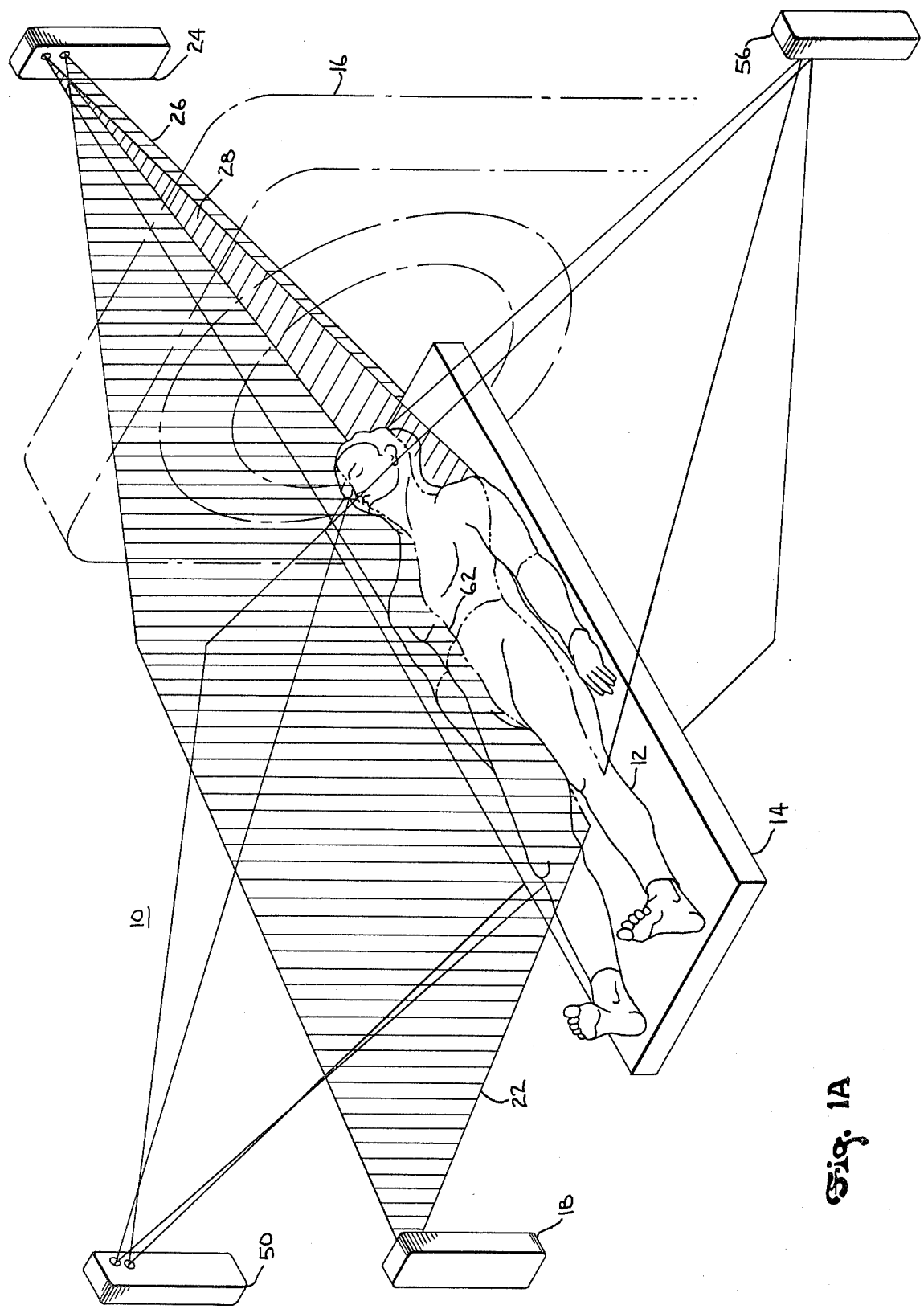
FIG. 1A is a perspective view of the patient orienting device of the present invention with the sagittal and a portion of the frontal plane shaded for emphasis.
Figure 1B:
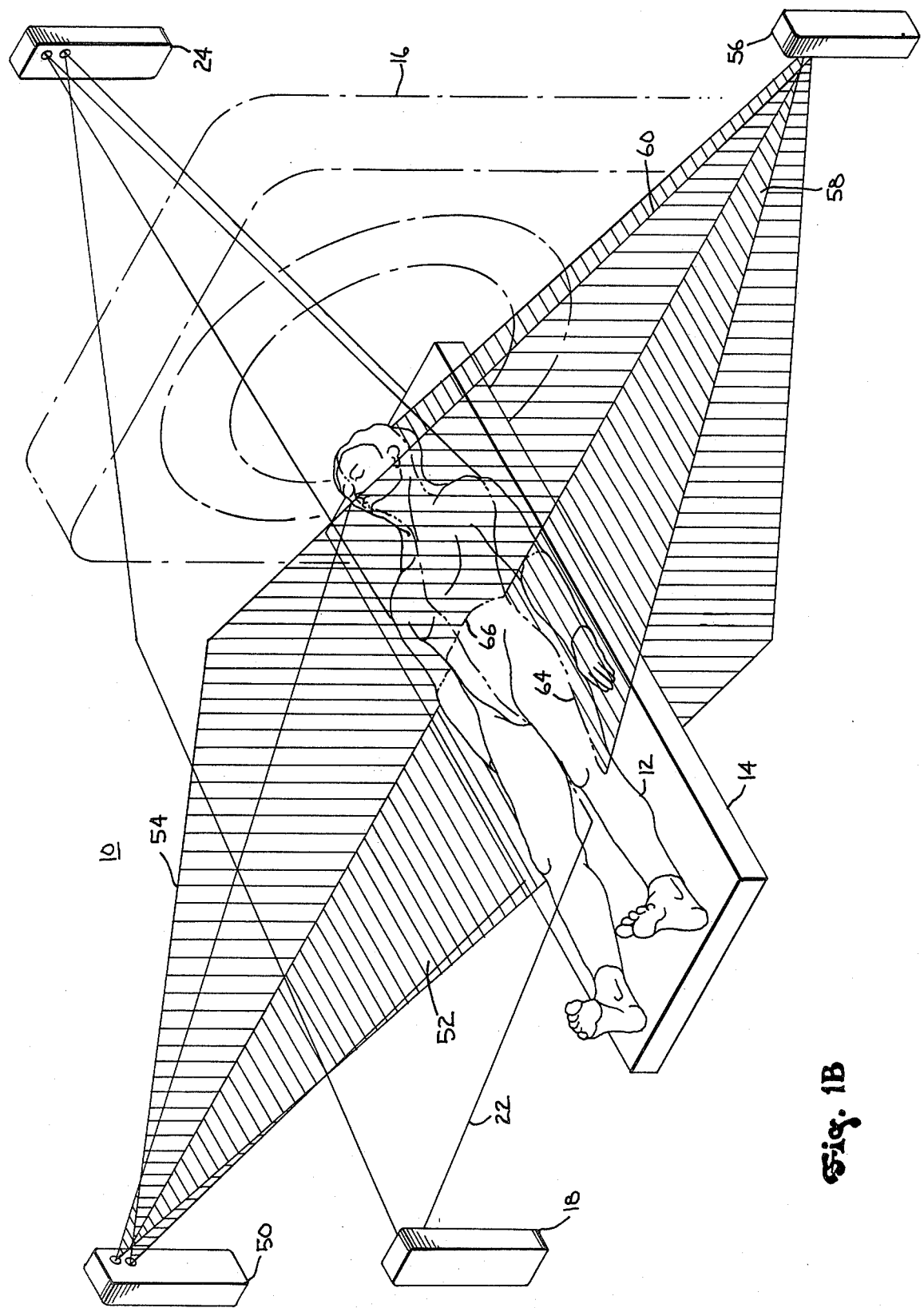
FIG. 1B is a perspective view, similar to FIG. 1A with additional portions of the frontal plane and the transverse plane shaded for emphasis.
Figure 2:
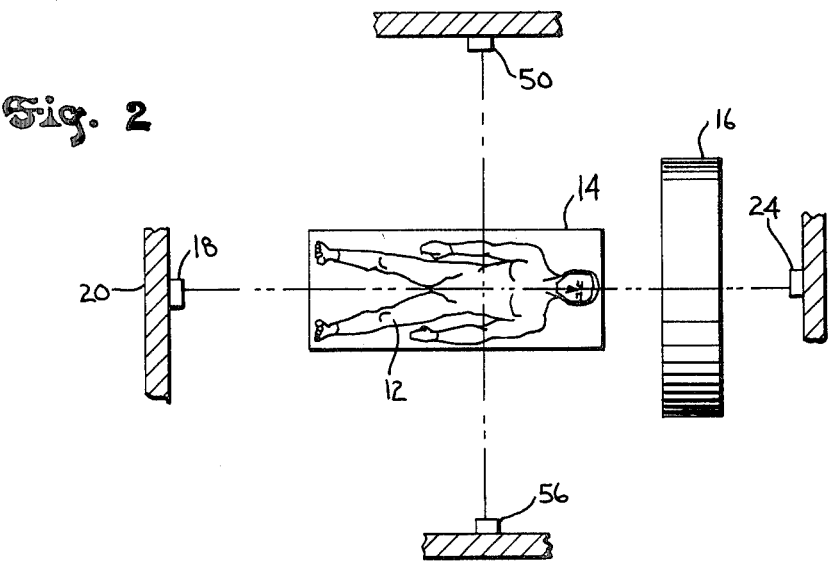
FIG. 2 is a plan view of the patient orienting device of the present invention showing the sagittal and transverse reference planes.

FIGS. 1A and 1B show patient orienting device 10 of the present invention. Patient orienting device 10 may be used in conjunction with patient 12 lying on table 14 to orient patient 12 with respect to radiological apparatus, such as tomographic imaging equipment 16 shown in phantom in the Figures. Radiological equipment 16 and table 14 are relatively movable to insert the portion of patient 12 to be scanned, for example, the head, in the radiation beam of tomographic imaging apparatus 16.

The patient orienting device of the present invention includes a first light source 18 which establishes a first plane of light 22 appliable to patient 12. Light source 18 is mounted on the wall 20 of the room containing radiological equipment 16 so that light plane 22 has a predetermined orientation. For example, light plane 22 may be a vertical plane. With respect to patient 12 lying on table 14, light plane 22 forms a reference plane corresponding to the sagittal plane of the body: that is, a vertical plane running from the head to the foot of the body from the chest through to the back of the body. As shown in FIG. 1, first light source 18 is typically positioned at the foot of the patient.

A second light source 24 is positioned on the wall at the opposite end of the sagittal plane from light source 18. Light source 24 provides two mutually perpendicular planes of light 26 and 28, termed herein the second and third light planes. Plane 26 is vertical and source 24 is positioned on the wall so that plane 26 is coplanar with plane 22 in the sagittal reference plane. Horizontal light plane 28 forms a reference plane corresponding to the frontal plane of the body: that is, a horizontal plane, when patient 12 is lying on table 14, taken from one side of the body through to the other.

Figure 3:
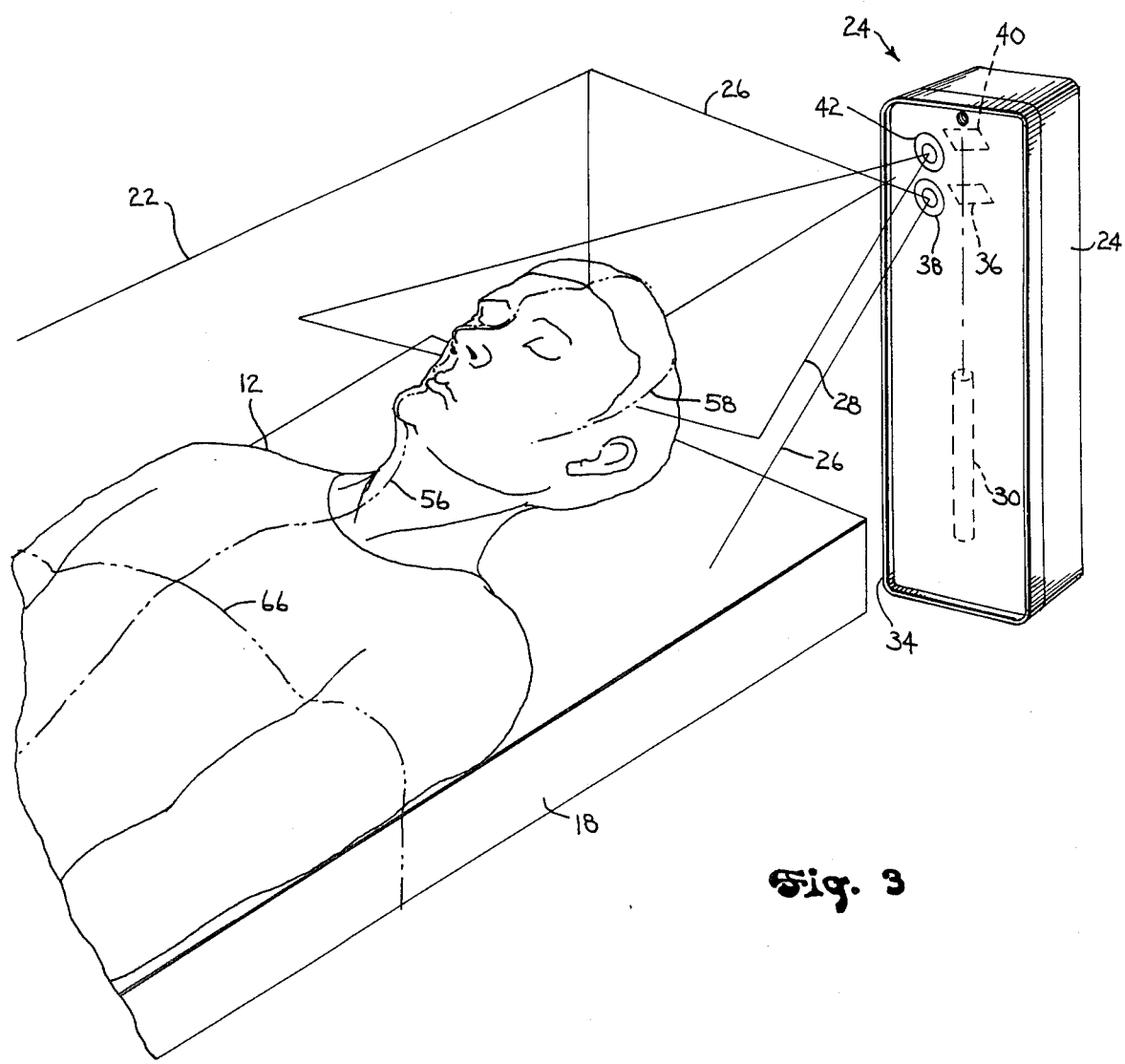
FIG. 3 is a perspective view of a light source suitable for use in the patient orienting device and the application of the planes of light to the patient.

FIG. 3 shows the details of one of the light sources employed in the patient orienting device 10, specifically light source 24. Light source 24 includes laser 30 mounted in cabinet 34. The light emitted from laser 30 strikes half-silvered mirror 36. The reflected light from half-silvered mirror 36 travels through anamorphic lens or line generator 38 which forms the beam of light into diverging rays which lie in vertical plane 26. The light passing through half-silvered mirror 36 strikes mirror 40. From mirror 40 the light travels through a second anamorphic lens 42 to produce horizontal light planes 28.

It will be appreciated that other types of radiant energy, such as infrared; other types of sources, such as incandescent; or other types of line generators, such as an aperture may be used. The foregoing terms are thus intended to include all suitable types and sources of radiant energy and line generators as may be used in the light source.

Third light source 50, similar to second light source 24, provides two additional light planes, 52 and 54, herein referred to as the fourth and fifth light planes. Light planes 52 and 54 are mutually perpendicular, light plane 52 being horizontal and light plane 54 being vertical. See FIG. 1B. Light source 50 is so positioned in the room that light planes 52 and 54 perpendicularly intersect light planes 22 and 26. The source is also positioned so that light plane 52 is coplanar with light plane 28 of light source 24 so that light plane 52 lies in the frontal reference planes. Light plane 54 forms a reference plane corresponding to the transverse plane of the body; that is, a vertical plane, with patient 12 lying on table 14, taken from side to side across the body.

A fourth light source 56, similar to second light source 24 provides two further light planes 58 and 60, herein referred to as the sixth and seventh light planes. Light planes 58 and 60 are mutually perpendicular with light plane 58 being horizontal and light plane 60 being vertical. Light source 56 is so positioned in the room that light planes 58 and 60 perpendicularly intersect light planes 22 and 26. The source is so positioned that light plane 58 is coplanar with light planes 28 and 52 so that light plane 58 lies in the frontal reference plane. The source is positioned so that light plane 60 is coplanar with light plane 54 from light source 50 to complete the transverse reference plane of the body.

In operation, light sources 18, 24, 50 and 56 are energized to provide light planes 22, 26, 28, 52, 54, 58 and 60. As shown in FIG. 1, this establishes a set of orthogonal reference planes corresponding to the sagittal, frontal and transverse anatomic planes of the body. The patient reclines on table 14 so that the light planes are applied to his/her body. The intersection of the light planes with the body forms luminous lines as shown in FIG. 1A, 1B and 3. The position of the patient is altered so that the patient is properly oriented with respect to the light planes. For example, the patient positioned so that light planes 22–26 run up the center of the body, as indicated by line 62 in FIG. 1A. The patient is similarly oriented in a desired manner with respect to light planes 28, 52, and 58 and light planes 54 and 60 forming the frontal and transverse reference planes, as indicated by luminous lines 64 and 66. When the orientation if complete, the patient may be moved into the path of radiation beam of equipment 16 and exposed to the necessary diagnostic or therapeutic radiation with the assurance that the patient is properly positioned for the most effective application of the radiation.

At least light planes 22, 26 and 28 will remain applied to the patient during exposure. Any displacement of that patient from the desired position may be easily detected from the pattern of the light planes on the body. For example, FIG. 3 shows the application of the 5 planes to the head of the patient, as for example, in preparation for making a neurological tomographic scan. Should the patient roll his/her head out of the desired position, the fact that luminous line 62 is no longer centered on the chin, nose, and forehead of the patient can be easily detected and corrected. Light planes 26 and 28 will also strike the sides of the head at non-symmetrical points, further indicating a rolling action. Lateral displacement of the head without rolling may also be detected by light planes 26 and 28.

Should the head of the patient be tilted about a vertical axis, as in a yawing movement, the luminous line of intersection 62 of plane 28 will be skewed across the face, noting this incorrect positioning. Similarly, rotation of the head about a horizontal axis, commonly called "pitch", will observed by displacement of the light planes 26 and 28. Thus, rotary and rectilinear displacement of the body from the desired position can be easily noticed and corrected with the orienting device of the present invention.

While in the foregoing embodiment of the invention, the orientation of the planes is fixed, in the embodiment of the invention shown in FIGS. 4 through 8, the relative position of one or more of the planes may be altered. This permits the orienting device to be used to establish the orientation of particular anatomical planes in the body. A typical use for the embodiment of the invention shown in FIGS. 4 through 8 is to establish the orientation of the plane of the base of the brain for use in neurological tomographic scans.

Figure 4:
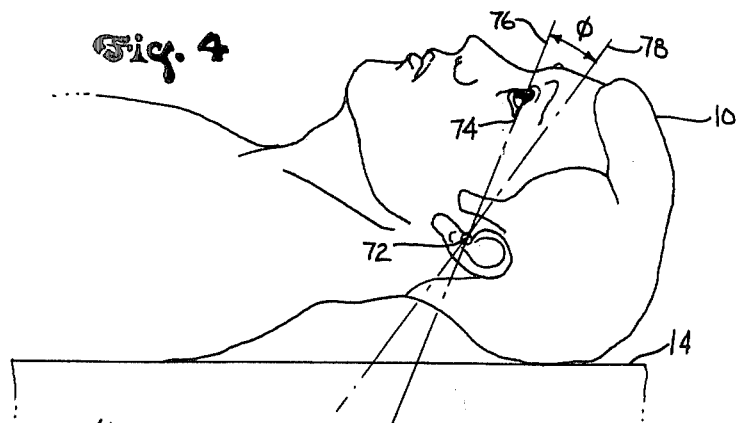
FIG. 4 is a lateral view of a human head, showing the orbital meatal plane and the plane of the base of the brain.

FIG. 4 shows a lateral view of a human head 70 lying on a generally horizontal surface, such as table 14. While the plane of the base of the brain cannot be determined from the exterior of the skull, this plane does bear a generally constant angle to other planes which can be determined from readily identifiable exterior anatomic landmarks. One such plane is a plane taken through the canal 72 of the ear and the lateral apex of the eye socket 74. This plane is often termed the "orbital meatal" or "optomeatal" plane 76. From anatomy it is known that the plane of the base of the brain 78 lies at a predetermined, generally constant angle $\phi$ with respect to the orbital meatal plane. As noted, in the past is has been difficult and time consuming to accurately position tomographic imaging apparatus for obtaining images parallel to the brain base plane 78.

Figure 5:
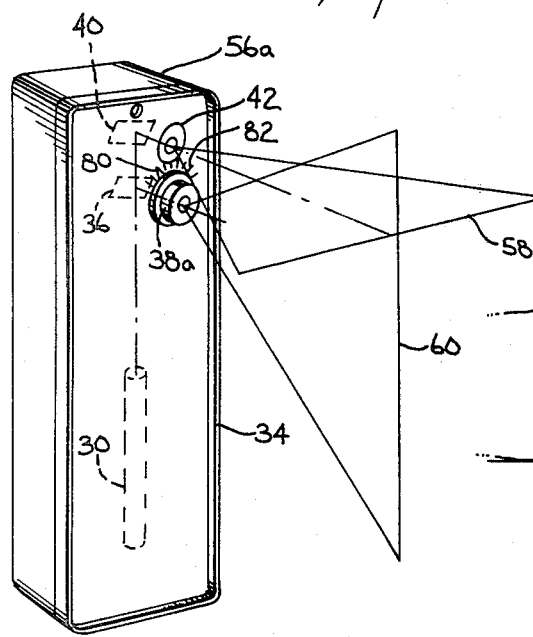
FIG. 5 is a perspective view of a light source means suitable for use in a modified embodiment of the present invention.

FIG. 5 shows the modified embodiment of the device of the present invention by which the orientation of plane 78 may be rapidly and accurately determined. In the modified embodiment, one of the light sources 50 or 56 has an anamorphic lens which is rotatably mounted in the cabinet of the light source, so that the plane of light generated by the lens may be rotated with respect to the other light plane provided by the light source. For example, in light source 56a, anamorphic lens 38a is rotatably mounted in cabinet 34. An indicator 80 is provided on line generating lens 38a for coaction with protractor scale 82 to indicate the angular relationship between light plane 60 and light plane 58.

In use, light source 56a is positioned adjacent the patient 12 with light planes 58 and 60 falling on the side of the patient's head to form luminous lines. Light source 56a is oriented with respect to some reference datum. This is typically done by utilizing light plane 58 and aligning it with a reference plane, for example, a horizontal plane parallel to the plane of horizontal table 14 upon which the patient is lying. Rotatable line generating lens 38a is rotated so that plane 60 is aligned with the ear canal 72 and the lateral eye apex 74, i.e. so that it lies along the orbital meatal plane. The amount of rotation required to obtain this alignement is noted by the coaction of pointer 80 with protractor scale 82 and is thus an indication of the angular orientation of the orbital meatal plane with respect to the horizontal reference plane. By applying a factor corresponding to the angular displacement $\phi$ of the brain base plane 78 from the orbital meatal plane 76, the angular orientation of the brain base plane can be quickly and easily determined.

Figure 6:
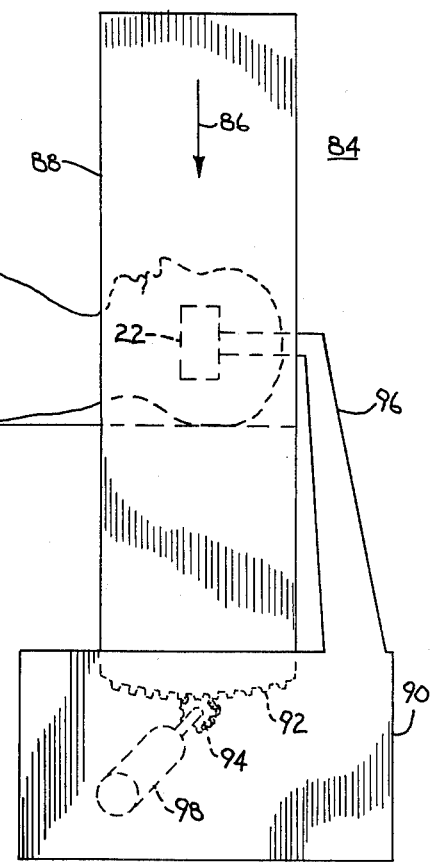
FIG. 6 is a side view showing use of the modified orienting means of the present invention in connection with tomographic imaging apparatus.

FIG. 6 shows the use of light source 56a in connection with tomographic imaging apparatus 84. Tomographic imaging apparatus 84 obtains X-ray images parallel to arrow 86 and perpendicular to the plane of the paper. The image producing portion 88 of apparatus 84 is so mounted on base 90 that the portion 88 may be tilted with respect to the base as by rack and pinion mechanism 92-94.

Light source 56a is mounted on the base 90 of imaging apparatus 84 as by arm 96 so that the planes of light may be applied to the side of the patient's head. The orientation of the orbital meatal plane is ascertained in the manner described above and the plane of the base of the brain determined. Rack and pinion mechanism 92-94 is operated as by a hand crank or motor 98 to tilt imaging portion 88 of tomographic imaging apparatus 84 so that the imaging axis as indicated by the arrow 86 lies parallel to the plane of the base of the brain. Apparatus 84 is then operated to obtain the images.

Figure 7:
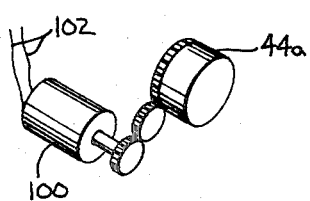
FIG. 7 is a partial perspective view of a further modification of the embodiment of the invention shown in FIG. 6 showing use of electromechanical signal generating means.

As shown in FIG. 7, rotatable line generating lens 38a may be coupled through gears to a synchro or shaft encoder 100 which provides a signal in conductors 102 indicative of the arcuate movement of lens 38a and the inclination of the orbital meatal plane. This signal may be provided to the control for motor 98 to obtain the tilting of imaging portion 88. The encoder 100 may provide an offset corresponding to the angular displacement $\phi$ between the brain's base plane and the orbital meatal plane.

Figure 8:
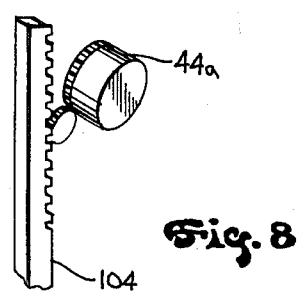
FIG. 8 is a partial perspective view of another modification of the embodiment of the invention shown in FIG. 6 showing use of mechanical signal generating means.

FIG. 8 shows a similar arrangement in which a mechanical signal such as the movement of shaft 104 is provided responsive to rotation of lens 38a to provide the signal indicative of the orbital meatal plane and usable to tilt imaging portion 88.

Various modes of carrying out the invention are contemplated as being within the scope of the following claims particularly pointing out and distinctly claiming the subject matter which is regarded as the invention.

I claim:

1. A device for orienting a body along first, second, and third intersecting reference planes, said device comprising:
   first light source means for establishing a first plane of light lying in said first reference plane and appliable to the body to be oriented;
   second light source means establishing second and third planes of light intersecting at a predetermined angle and applicable to the body, said second plane of light being coplanar with said first light plane, said third plane of light lying in said second reference plane;

a third light source means establishing fourth and fifth planes of light intersecting at a predetermined angle and appliable to the body, said third light source means lying to one side of said first and second light planes and intersecting said light planes at a predetermined angle, said fourth light plane being coplanar with said third light plane and said fifth light plane lying in said third reference plane; and a fourth light source for establishing sixth and seventh light planes intersecting at a predetermined angle and appliable to the body, said fourth light source lying to the opposite side of said first and second light planes from said third light source means and establishing said sixth and seventh light planes so that they intersect said first and second light planes at a predetermined angle, said sixth light plane being coplanar with said third and fourth light planes and said seventh light plane being coplanar with said fifth light plane.

2. The device according to claim 1 wherein the intersecting reference planes are mutually perpendicular and wherein said second and third, fourth and fifth, and sixth and seventh light planes perpendicularly intersect each other and wherein said fourth and fifth light planes and said sixth and seventh light planes intersect said first and second light planes normal to the latter.

3. The orienting device according to claim 1 further defined as a device for orienting a patient with respect to said reference planes.

4. The orienting device according to claim 3 further defined as a device for determining the orientation of a plane defined by anatomical landmarks on the patient with respect to a reference datum, wherein one of said third and fourth light sources bears a known relationship to said reference datum, one of said light planes of said sources being arcuately movable to a position in which it lies along said anatomical landmark plane, and wherein said orienting device includes means for ascertaining the amount of arcuate movement of said one light plane.

5. The orienting device according to claim 4 wherein the other plane of said third or fourth light sources is aligned with a reference plane to establish the relationship of the light source to the reference datum.

6. The orienting device of claim 5 further defined as means for determining the orientation of the orbital meatal plane of the patient with respect to a reference plane.

7. The orienting device according to claim 4 wherein said light source means providing said arcuately movable light plane is further defined as having a rotatable element for arcuately moving said one light plane and wherein said ascertaining means is responsive to the rotation of said rotatable element.

8. The orienting device according to claim 6 further defined as a device for determining the orientation of the plane of the base of the brain, wherein said ascertaining means includes means for altering the ascertainment obtained from said ascertaining means by a factor corresponding to the displacement of the brain base plane from the orbital meatal plane.

9. The orienting device according to claim 8 further defined as a device for positioning tomographic imaging apparatus with respect to the plane of the base of the brain wherein said tomographic imaging apparatus has signal responsive positioning means and wherein said ascertainment means provides a signal responsive to the arcuate movement of said second light plane to said signal responsive positioning means of said tomographic imaging apparatus.

10. The orienting device according to claim 4 further defined as a device for positioning tomographic imaging apparatus with respect to the patient, wherein said tomographic imaging apparatus has signal responsive positioning means and wherein said ascertaining means provides a signal responsive to the arcuate movement of said one light plane to said signal responsive positioning means of said tomographic imaging apparatus.

11. The orienting device according to claim 9 or 10 wherein said ascertaining means provides a mechanical signal.

12. The orienting device according to claim 9 or 10 wherein said ascertaining means provides an electrical signal.

* * * * *